United States Patent [19]

Klein et al.

[11] 4,045,499
[45] Aug. 30, 1977

[54] PROCESS FOR THE PREPARATION OF 1,1,3,3-SUBSTITUTED HYDROXY INDANES

[75] Inventors: Alfons Klein, Duesseldorf; Karlfried Wedemeyer, Cologne, both of Germany

[73] Assignee: Bayer Aktiengesellschaft, Leverkusen, Germany

[21] Appl. No.: 516,945

[22] Filed: Oct. 22, 1974

[30] Foreign Application Priority Data

Nov. 14, 1973 Germany .................... 2356813

[51] Int. Cl.² .......................................... C07C 37/00
[52] U.S. Cl. ........................ 260/621 R; 260/611 F; 260/619 R; 260/619 A; 260/619 B; 260/619 D; 260/619 F; 260/620; 260/623 R; 260/624 R; 260/626 R; 260/626 T
[58] Field of Search .......... 260/621 R, 619 F, 626 R, 260/626 T, 624 R, 620, 619 D, 619 A, 619 B, 619 R, 613 R, 611 F, 623 R

[56] References Cited

U.S. PATENT DOCUMENTS

| | | | |
|---|---|---|---|
| 1,972,599 | 9/1934 | Perkens et al. | 260/621 D |
| 2,091,565 | 8/1937 | Perkens et al. | 260/621 D |
| 2,109,015 | 2/1938 | Mederl et al. | 260/621 R |
| 2,265,583 | 12/1941 | Stevens et al. | 260/621 D |
| 2,948,704 | 8/1960 | Morris | 260/621 R |
| 3,057,929 | 10/1962 | Arrigo | 260/621 R |
| 3,644,540 | 2/1972 | Wood et al. | 260/626 R |
| 3,954,889 | 5/1976 | Klein et al. | 260/619 R |

FOREIGN PATENT DOCUMENTS

| | | | |
|---|---|---|---|
| 2,304,588 | 8/1974 | Germany | 260/621 R |

*Primary Examiner*—Norman Morgenstern
*Attorney, Agent, or Firm*—Burgess, Dinklage & Sprung

[57] ABSTRACT

1,1,3,3-substituted hydroxy indanes having the formula

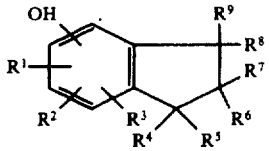

wherein
$R^1$, $R^2$ and $R^3$, which may be the same or different, are selected from the group of hydrogen, halogen and optionally substituted alkyl, cycloalkyl, aralkyl and aryl, in addition to which
$R^2$ and $R^3$, when they are in the ortho position relative to one another, may be taken together with the carbon atoms of the benzene ring to which they are attached to form a 5 membered carbocyclic ring,
$R^4$ is

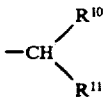

wherein
$R^{10}$ and $R^{11}$, which may be the same or different, are selected from the group of hydrogen and optionally substituted alkyl, cycloalkyl, aralkyl and aryl, and
$R^5$, $R^6$, $R^7$, $R^8$ and $R^9$, which may be the same or different, are selected from the group of optionally substituted alkyl, cycloalkyl, aralkyl and aryl, the arrangement being such that
$R^5$ and $R^{10}$ and/or
$R^6$ and $R^7$ and/or
$R^8$ and $R^9$ may form together with the carbon atoms to which they are attached a cycloaliphatic ring in addition to which
$R^6$ and/or $R^7$ may also represent hydrogen.

9 Claims, No Drawings

PROCESS FOR THE PREPARATION OF 1,1,3,3-SUBSTITUTED HYDROXY INDANES

BACKGROUND

This invention relates to 1,1,3,3-substituted hydroxy indanes and to processes for their production.

It is known that 4,6-diisopropyl-1,1-dimethyl-5-hydroxy indane may be obtained by reacting 2,6-di-isopropylphenol with isoprene in the presence of an acid catalyst (British Pat. No. 1,199,695). It is also known that 4-hydroxy indanes may be obtained by rearranging chromanes with molar quantities of aliminium chloride (U.S. Pat. No. 3,057,929).

Unfortunately, these known processes cannot be generally applied, and it is only the special hydroxy indanes referred to above that can be produced by them.

SUMMARY

New 1,1,3,3-substituted hydroxy indanes have now been found, corresponding to the following general formula:

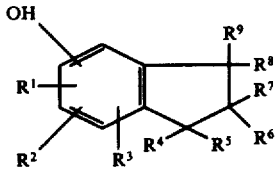
(I)

in which
$R^1$, $R^2$ and $R^3$ are the same or different and represent hydrogen, halogen or an optionally substituted alkyl, cycloalkyl, aralkyl or aryl radical, in addition to which
$R^2$ and $R^3$, when they are in the o-position to one another, may form an anellated carbocyclic 5-ring with the carbon atoms of the benzene ring substituted by them, $R^4$ represents the group

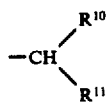

where $R^{10}$ and $R^{11}$ are the same or different and represent hydrogen, an optionally substituted alkyl, cycloalkyl, aralkyl or aryl radical, and
$R^5$, $R^6$, $R^7$, $R^8$ and $R^9$ are the same or different and represent an optionally substituted alkyl, cycloalkyl, aralkyl or aryl radical, the arrangement being such that
$R^5$ and $R^{10}$ and/or
$R^6$ and $R^7$ and/or
$R^8$ and $R^9$ may form a cycloaliphatic ring together with the carbon atoms substituted by them, in addition to which
$R^6$ and/or $R^7$ may also represent hydrogen.

DESCRIPTION

More particularly, the new 1,1,3,3-substituted hydroxy indanes correspond to the following general formula:

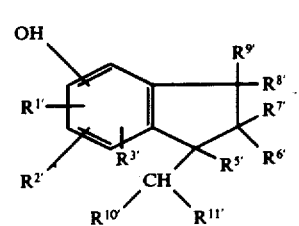
(Ia)

in which
$R^{1'}$, $R^{2'}$ and $R^{3'}$ are the same or different and represent hydrogen, halogen or an alkyl radical with up to 6 carbon atoms,
$R^{5'}$, $R^{6'}$, $R^{7'}$, $R^{8'}$ and $R^{9'}$ are the same or different and represent an alkyl radical with up to 6 carbon atoms, in addition to which $R^{6'}$ and/or $R^{7'}$ can also represent hydrogen, and
$R^{10'}$ and $R^{11'}$ represent hydrogen, in addition to which $R^{5'}$ and $R^{10'}$ together may also represent the group

$-(CH_2)-_x$ where x is the number 4 or 5.

More particularly, these new compounds correspond to the following general formula:

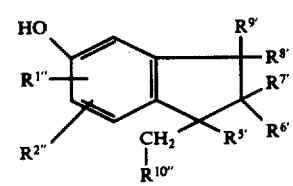
(Ib)

in which
$R^{1''}$ and $R^{2''}$ are the same or different and represent hydrogen, chlorine or an alkyl radical with up to 4 carbon atoms,
$R^{5'}$, $R^{6'}$, $R^{7'}$, $R^{8'}$ and $R^{9'}$ are the same or different and represent an alkyl radical with up to 6 carbon atoms, in addition to which
$R^{6'}$ and/or $R^{7'}$ may also represent hydrogen, and
$R^{10''}$ represents hydrogen, in addition to which
$R^{5'}$ and $R^{10''}$ together may also represent the group

$-(CH_2)_x-$
in which x is the number 4 or 5.

More particularly, the new compounds correspond to the following general formula

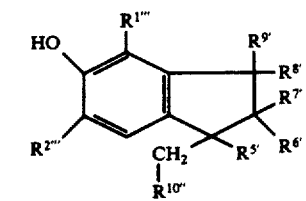
Ic in which
$R^{1'''}$ and $R^{2'''}$ are the same or different and represent hydrogen, alkyl with up to 4 carbon atoms, preferably methyl or ethyl or chlorine,
$R^{5'}$, $R^{6'}$, $R^{7'}$, $R^{8'}$ and $R^{9'}$ are the same or different and represent an alkyl radical with up to 6 carbon atoms, in addition to which $R^{6'}$ and/or $R^{7'}$ may also represent hydrogen, and
$R^{10''}$ represents hydrogen, in addition to which
$R^{5'}$ and $R^{10''}$ together may also represent a tetramethylene or pentamethylene radical.

In the new compounds according to the invention:
Halogens are fluorine, chlorine, bromine, iodine; preferably chlorine and bromine:

Optionally substituted alkyl radicals are linear and branched alkyl radicals with up to 12, preferably with up to 8, more particularly with up to 4 carbon atoms, for example methyl, ethyl, propyl, isopropyl, butyl, isobutyl, t-butyl, amyl, isoamyl, the isomeric hexyl, heptyl and octyl radicals, preference being given to methyl, ethyl, propyl, isopropyl, butyl, isobutyl, t-butyl, amyl, isoamyl and hexyl radicals.

Optionally substituted cycloalkyl radicals are those with 3 to 8 carbon atoms, preferably the cylopentyl and cyclohexyl radicals:

Optionally substituted aralkyl radicals are those with up to 6 carbon atoms in the aliphatic portion and with up to 14 carbon atoms in the aromatic proton with methyl, propyl, isopropyl, butyl, isobutyl, pentyl and hexyl being mentioned by way of example for the aliphatic portion, and phenyl, naphthyl. anthryl being mentioned by way of example for the aromatic portion; benzyl and ethylphenyl represent preferred araliphatic radicals:

Optionally substituted aryl radicals are, for example, phenyl, naphthyl, anthryl, preferably phenyl:

Substituents of the optionally substituted cycloalkyl, aralkyl and aryl radicals are, for example, alkyl radicals with up to 12 carbon atoms, preferably with up to 6 carbon atoms, which may be linear or branched, such as methyl, ethyl, propyl, isopropyl, butyl, t-butyl.

It has also been found that the new 1,1,3,3-substituted hydroxy indanes can readily be obtained by reacting alkylphenols corresponding to the general formula:

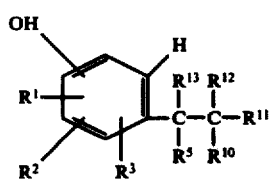

(II)

in which
$R^1$, $R^2$, $R^3$, $R^5$, $R^{10}$ and $R^{11}$ are as defined above,
$R^{12}$ represents hydrogen, and
$R^{13}$ represents halogen, hydroxyphenyl or the group —$OR^{14}$ where $R^{14}$ is hydrogen or an optionally substituted alkyl, cycloalkyl, aralkyl or aryl radical, in addition to which
$R^{12}$ and $R^{13}$ together may also represent another bond between the carbon atoms substituted by them,
with olefins in which at least one double-bonded carbon atom exclusively contains carbon-carbon bonds, in other words compounds containing the group

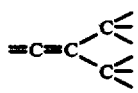

or with compounds which yield the corresponding olefin in situ, in the presence of acid catalysts at temperatures in the range from 70° to 360° C.

The reaction is preferably carried out at temperatures in the range from 100° to 250° C, more particularly at temperatures in the range from 110° to 200° C.

In general, the acid catalysts used for the process according to the invention can be the same acid catalysts known per se and used in known manner for the alkylation of phenols (cf. DAS No. 1,518,460; DOS No. 1,643,390; DOS No. 2,034,369; DOS No. 2,111,193).

Examples of acid catalysts of this kind are Lewis acids such as $AlCl_3$, $BF_3$; proton acids, i.e. acids whose dissociation is accompanied by the release of a proton, more especially mineral acids such as a sulphuric acid, phosphoric acid, hydrochloric acid and perichloric acid, but also, and in particular, aromatic sulphonic acids such as benzene and toluene sulphonic acids; silica and fuller's earth such as montmorillonite, silicoaluminates and silica gel. Silicas are finely divided materials containing silicic acid and/or aluminum oxide. The silicas and fuller's earths can be used either without any pretreatment or after activation treatment with mineral acids such as sulphuric acid, phosphoric acid, hydrochloric acid, perchloric acid or hydrofluoric acid. Natural or synthetic ion exchangers such as zeolites or exchanger resins may also be used. Exchanger resins are insoluble resins consisting of inert 2-dimensionally or 3-dimensionally crosslinked polymers which are substituted by reactive groups such as phosphoric, phosphonic, sulphuric or sulphonic acid groups.

Mineral acids, fuller's earths and silicas and also exchanger resins may be used with advantage in the process according to the invention.

Preferred mineral acids are sulphuric acid, hydrochloric acid and phosphoric acid.

Of the silicas and fuller's earths, it is preferred to use those which have been activated by treatment with an acid in known manner (Chemie fur Labor and Betrieb, 1956, page 422; Ullmann, 3rd Edition, Vol. 9, pages 271 et seq; Vol. 8, pages 801 to 804).

Suitable ion exchangers are, in particular, styrenedivinylbenzene resins, crosslinked styrene resins, phenol-formaldehyde resins and benzene-formaldehyde resins, all preferably substituted by sulphonic acid groups. It is particularly preferred to use resins of the kind containing one sulphonic acid group oer 0.5 to 2 monomer units of the resin (Ullmann, 3rd Edition, Vol. 8, pages 806 to 822, in particular page 816; DT-PS 915,267).

It is also possible to use mixtures of the aforementioned catalysts.

The quantity of catalyst used in the process according to the invention may be varied within a wide range. The catalyst is generally used in a quantity of from about 2 to 30% by weight and preferably in a quantity of from 7 to 14% by weight, based on the alkylphenol of formula (II).

Alkylphenols of the general formula (II) which can be used as starting materials for the process according to the invention are known.

They can correspond to the following general formula:

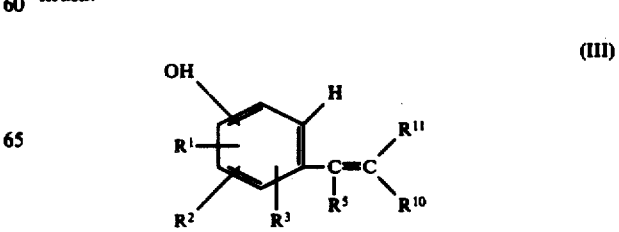

(III)

in which $R^1$, $R^2$, $R^5$, $R^{10}$ and $R^{11}$ are as defined above. Examples of these alkylphenols are 4-isopropenyl phenol, 2-methyl-4-isopropenyl phenol, 2,6-dimethyl-4-isopropenyl phenol, 2-chlor-4-isopropenyl phenol, 2,6-dichlor-4-isopropenyl phenol. They can also correspond to the following general formula:

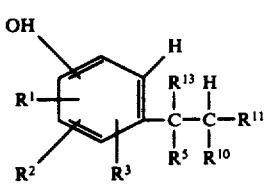

(IV)

in which $R^1$, $R^2$, $R^3$, $R^5$, $R^{10}$, $R^{11}$ and $R^{13}$ are as defined above. Examples of these alkyl-phenols are 2-(4-hydroxyphenyl)-2-propanol, 2-(4-hydroxy-3-methylphenyl)-2-propanol, 2,-(4-hydroxy-3,5-dimethylphenyl)-2-propanol, 2-(4-hydroxy-3-chlorphenyl)-2-propanol, 2-(4-hydroxy-3,5-dichlorphenyl)-2-propanol, 2-methoxy-2-(4-hydroxyphenyl)-propane, 2-methoxy-2-(4-hydroxy-3-methylphenyl)-propane, 2-methoxy-2-(4-hydroxy-3,5-dimethylphenyl)propane, 2-methoxy-2-(4-hydroxy-3-chlorphenyl)-propane, 2-methoxy-2-(4-hydroxy-3,5-dichlorphenyl)-propane.

Other suitable compounds of the general formula (II) are the dimers of the alkylphenols of the general formula (III) which correspond to the general formula:

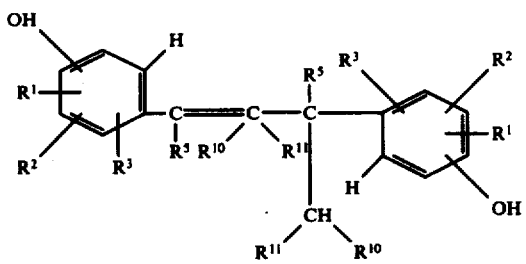

(V)

in which $R^1$, $R^2$, $R^3$, $R^5$, $R^{10}$ and $R^{11}$ are as defined above, also their trimers which correspond to the general formula:

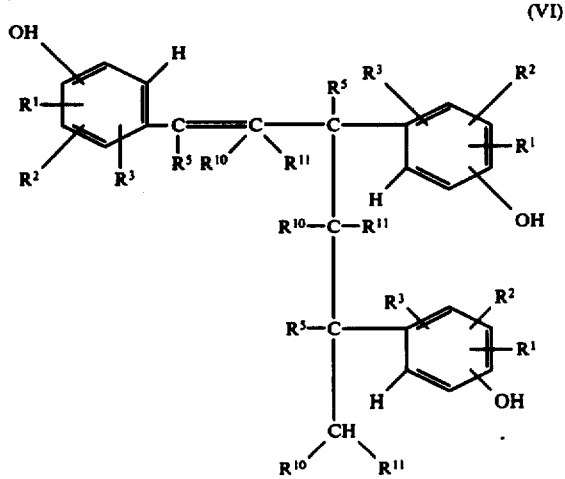

(VI)

in which $R^1$, $R^2$, $R^3$, $R^5$, $R^{10}$ and $R^{11}$ are as defined above.

Particularly suitable compounds of general formulae (V) and (VI) are dimers and trimers of the optionally substituted propenylphenol corresponding to the general formulae:

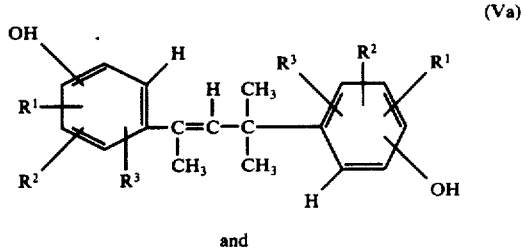

(Va)

and

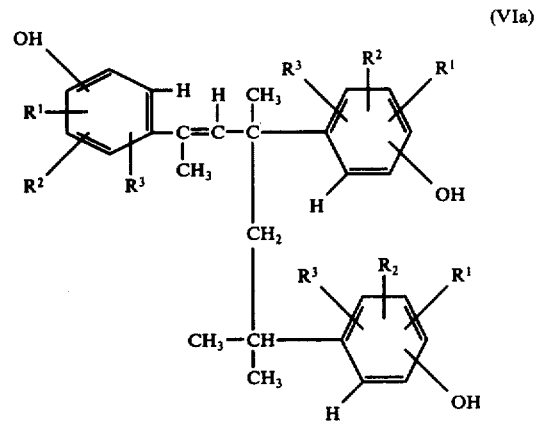

(VIa)

in which $R^1$, $R^2$ and $R^3$ are as defined above.

Another group of alkylphenols of the general formula (II) which can be used in the process according to the invention are compounds corresponding to the general formula:

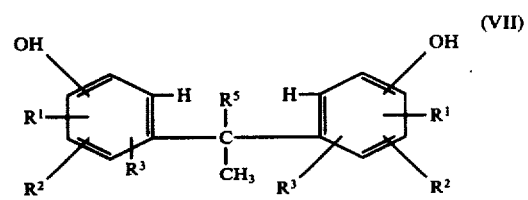

(VII)

in which $R^1$, $R^2$, $R^3$ and $R^5$ are as defined above. Examples of these compounds include 2,2-bis-(4-hydroxyphenyl)-propane, 2,2-bis-(3-methyl-4-hydroxyphenyl)-propane, 2,2-bis-(3,5-dimethyl-4-hydroxyphenyl)-propane, 2,2-bis-(3-chlor-4-hydroxyphenyl)-propane, 2,2-bis-(4-hydroxyphenyl)-butane, 1,1-bis-(4-hydroxyphenol)-1-phenylethane.

Other examples of alkylphenols of the general formula (II) which may be used in the process according to the invention are 1,1-bis-(4-hydroxyphenyl)-cyclohexane and 1,1-bis-(4-hydroxyphenyl)-cyclopentane.

The olefins containing the group

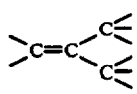

i.e. in which at least one double-bonded carbon atom contains only carbon-carbon bonds, the so-called "tertiary" olefins, are also known. The following are mentioned by way of example: 2-methylpropene, 2-methyl-1-butene, 2-methyl-2-butene, 2,3-dimethyl-1-butene, 2,3-dimethyl-2-butene, 2-methyl-2-phenyl-1-propene, 2,4,4-trimethyl-1-pentene, 2,4,4-trimethyl-2-pentene.

It is preferred to use 2-methylpropene (isobutylene) and a mixture of 2,4,4-trimethyl-1-pentene and 2,4,4-trimethyl-2-pentene (diisobutylene).

The molar ratio between the alkylphenol of general formula (II) and the tertiary olefin may be varied within wide limits. Although the phenol and the olefin can be used in a substantially equimolar ratio, it is preferred to use a ratio of about 2 mols to about 7 mols of olefin per mol of phenol. At the same time, the phenol nucleus may be substituted by one or more alkyl groups corresponding to the tertiary olefin used.

These tertiary alkyl groups may optionally be removed again by known methods, such as dealkylation in the presence of acid catalysts, or transalkylation by the addition of phenol.

The process according to the invention may be carried out at normal pressure or at elevated pressures of up to 60 atmospheres, preferably up to 20 atmospheres.

More particularly the process according to the invention is carried out at pressures in the range from 1 to 10 atmospheres.

The process according to the invention may also be carried out in an inert solvent or diluent such as, for example, aliphatic and aromatic hydrocarbons, especially hexane and heptane, benzene, toluene and xylene.

In general, the process acccording to the invention is carried out by initially introducing the alkylphenol of formula (II) optionally in solution in an inert solvent, into a suitable reaction vessel, for example an autoclave, adding the catalyst selected, heating the mixture to the reaction temperature selected, adding the olefin with stirring and subsequently leaving the mixture to react with stirring for about 0.5 to about 5 hours.

It is also possible to carry out the process according to the invention by putting the selected catalyst, optionally dissolved or suspended in an inert solvent in a suitable reaction vessel, e.g. an autoclave, heating to the chosen reaction temperature, adding the alkyl phenol of the general formula II and the chosen olefin, whilst simultaneously stirring over a period lasting from about 0.5 to about 5 hours and finally reacting for a further 0.5 to about 5 hours whilst stirring.

On completion of the reaction, the reaction product is worked up in known manner by removing the catalyst from the reaction vessel by known methods such as, for example, filtration, centrifuging and washing, depending upon the type of catalyst used, and isolating the reaction products from the catalyst-free reaction mixture, again in known manner, for example by distillation or crystallisation.

The process according to the invention may also be carried out continuously in a homogeneous phase using fixed-bed or fluidised-bed catalysts. The apparatus used for carrying out the process according to the invention may be any one of a number of forms known from the prior art.

The process according to the invention as applied, for example, to the reaction of isobutylene with 4-isopropenylphenol is illustrated by the following reaction scheme for the use of the alkylphenols of general formula (III):

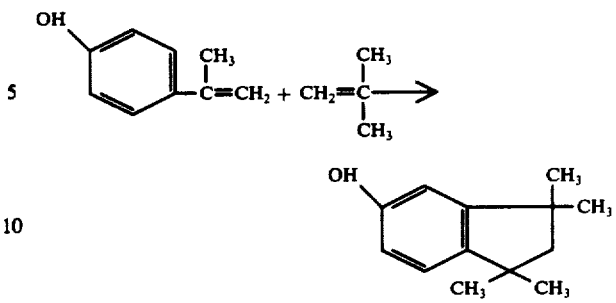

In cases where alkylphenols of formula (II), in which $R^{12}$ and $R^{13}$ do not together represent another bond between the carbon atoms substituted by them, i.e. compounds of general formula (IV), are used in the process according to the invention, the radical $R^{13}$ is split off during the reaction together with the hydrogen of the aliphatic carbon atom in the α-position. This is explained by the following reaction scheme relating by way of example to 2,2-bis-(4-hydroxyphenyl)propane:

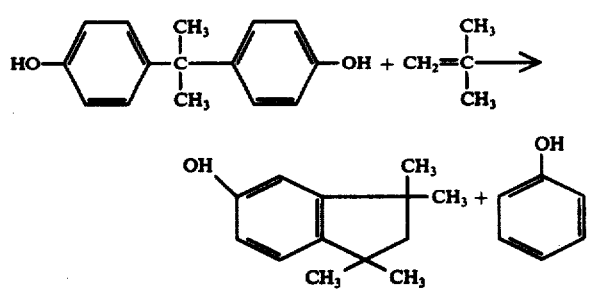

Instead of using the tertiary olefin, it is also possible to employ compounds of the kind which yield the corresponding olefin in situ during the reaction, for example the corresponding alcohols or tertiary alkylphenols.

Examples of the alcohols which may be used as starting materials instead of the corresponding phenols in the process according to the invention are isobutanol, tert.-butanol and 2-methyl-2-butanol.

In addition, the alkylphenols of general formula (II) can be reacted with phenols substituted by one or more tertiary alkyl groups instead of being reacted with the corresponding tertiary olefins. The tertiary olefin is yielded in situ by the tertiary alkyl group. For example, phenol is formed in addition to the reaction product according to the invention, namely 1,1,3,3-tetramethyl-5-hydroxy indane, by reacting 4-isopropenylphenol and 4-tert.-butylphenol by the process according to the invention thus demonstrating that the isobutylene is yielded in situ by the 4-tert.-butylphenol in accordance with the following scheme:

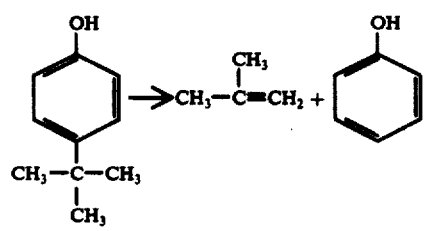

Examples of phenols substituted by tertiary alkyl groups are o-, m- and p-tert.-butylphenol, 2,4-di-tert.-butylphenol, 3,5-di-tert.-butylphenol.

In another embodiment of the process according to the invention, it is possible to use alkylphenols of the general formula (II) which are simultaneously substituted by one or more tertiary alkyl groups, i.e. in which one or more of the radicals $R^1$, $R^2$ and $R^3$ represent a tertiary alkyl group, both as the alkylphenol of general formula (II) and also instead of the corresponding tertiary olefin. In this case, the reaction according to the invention is intramolecular.

The following are mentioned as examples of starting compounds substituted by tertiary alkyl groups, i.e. alkylphenols of general formula (II): 2-tert.-butyl-4-isopropenylphenol, 2,6-di-tert.-butyl-4-isopropenylphenol, 2-methyl-6-tert.-butyl-4-isopropenylphenol, 2-ethyl-6-tert.-butyl-4-isopropenylphenol, 2-isopropyl-6-tert.-butyl-4-isopropenylphenol, 2-cyclopentyl-6-tert.-butyl-4-isopropenylphenol, 2-(4-hydroxy-3-tert.-butylphenol)-2-propanol, 2-(4-hydroxy-3,5-di-tert.-butylphenol)-2-propanol, 2-(4-hydroxy-3-methyl-5-tert.-butylphenol)-2-propanol; 2-methoxy-2-(4-hydroxy-3-tert.-butylphenyl)-propane, 2-methoxy-2-(4-hydroxy-3,5-di-tert.-butylphenyl)-propane, 2-methoxy-2-(4-hydroxy-3-methyl-5-tert.-butylphenyl)-propane, 2,2-bis-(4-hydroxy-3-tert.-butylphenyl)-propane, 2,2-bis-(4-hydroxy-3,5-di-tert.-butylphenyl)-propane, 2,2-bis-(4-hydroxy-3-methyl-5-tert.-butylphenyl)-propane, 2,2-bis-(4-hydroxy-3-tert.-butylphenyl)-butane, 1,1-bis-(4-hydroxy-3-tert.-butylphenyl)-cyclohexane, 1,1-bis-(4-hydroxy-3-tert.-butylphenyl)-cyclopentane, 1,1-bis-(4-hydroxy-3-tert.-butylphenyl)-1-phenyl ethane.

It is also possible to prepare the alkylphenols of the formula (II) simultaneously substituted by one or more tertiary alkyl groups, providing they correspond to general formula (VII), by a one-pot process from an optionally substituted phenol in a first reaction stage, and to react them immediately afterwards in a second stage to form the hydroxy indanes by the process according to the invention.

If a corresponding alcohol is used instead of the tertiary olefin, the process according to the invention may be carried out by initially introducing the alkylphenol of the formula (II) and the catalyst, optionally in solution in an inert solvent, into the reaction vessel and introducing the alcohol over a period of about 0.5 to about 5 hours. The reaction temperature is preferably selected in such a way that the water of reaction which forms is continuously distilled off or is distilled off azeotropically by means of the inert solvent. The reaction mixture is then left to react for about another 0.5 to about 5 hours at the temperature selected.

It is also possible to introduce the catalyst selected, optionally in solution and/or suspension in an inert solvent, initially into the reaction vessel and then to introduce the alkylphenol of the formula (II) used as starting compound and the alcohol selected simultaneously with stirring over a period of about 0.5 to about 5 hours, and at the same time to distil off the water of reaction which forms either continuously or azeotropically with the inert solvent. The reaction mixture is then left to react for about another 0.5 to 5 hours at the reaction temperature.

If the phenol substituted by one or more corresponding tertiary alkyl groups is used instead of the tertiary olefin, the process according to the invention can be carried out by initially introducing the corresponding tertiary alkylphenol which yields the tertiary olefin in situ and the alkylphenol of formula (II) used as starting compound, optionally in solution in an inert solvent, into the reaction vessel, adding the catalyst selected, heating the mixture to the reaction temperature selected and leaving it to react while stirring for about 0.5 to about 5 hours.

It is also possible to introduce the catalyst selected, optionally dissolved and/or suspended in an inert solvent, initially into the reaction vessel, for example an autoclave, to heat it to the reaction temperature selected and to introduce the starting compound of formula (II) selected and the tertiary alkylphenol which yields the tertiary olefin in situ, simultaneously with stirring over a period of about 0.5 to about 5 hours, and then to leave the mixture to react with stirring for about another 0.5 to about 5 hours.

If, as described above, alkylphenols of general formula (VII) which are substituted by one or more tertiary alkyl groups, i.e. which are simultaneously used as the second reaction component instead of the tertiary olefin, are used, the process according to the invention is carried out as follows.

The alkylphenol of formula (II) substituted by one or more tertiary alkyl groups, optionally in solution and/or suspension in an inert solvent, is initially introduced into the reaction vessel, the catalyst selected is added and the mixture heated with stirring to the reaction temperature selected at which it is left to react for about another 0.5 to about 5 hours.

It is also possible to prepare alkylphenols of formula (VII) simultaneously substituted by one or more tertiary alkyl groups, in a one-pot process from a correspondingly substituted phenol in a first reaction stage, and to react them immediately afterwards in a second stage to form the 1,1,3,3-substituted hydroxy indanes by the process according to the invention. For example, the following procedure may be adopted:

The alkylphenol of formula (VII) is initially introduced into the reaction apparatus, optionally in solution and/or suspension in an inert solvent, and the catalyst subsequently added. The tertiary olefin used is then introduced with stirring over a period of about 0.5 to about 5 hours, depending on the size of the batch, at a temperature of from about 40° to about 70° C and at normal or elevated pressure, preferably at a pressure of up to about 60 atmospheres, more particularly at a pressure of up to about 10 atmospheres. On completion of alkylation, the temperature is increased to the reaction temperature selected for the process according to the invention and the same tertiary olefin or another tertiary olefin subsequently added in the second stage in accordance with the above general description and the process according to the invention is carried out.

Since a tertiary olefin is used in the first stage, i.e. for alkylating the phenol, the tert.-alkylated phenol may be simultaneously used instead of the tertiary olefin in the second stage and the process according to the invention carried out in accordance with the above general description without further addition of a tertiary olefin.

The new hydroxy indanes are valuable intermediate products, more especially for the synthesis of insecticides, germicides or fungicides and may themselves be used as odorants and antioxidants (British Pat. No. 1,199,695, U.S. Pat. No. 2,057,929).

By virtue of their reducing action, the new hydroxy indanes may be used in known manner as developers in photographic materials and processes.

More particularly the new hydroxy indanes may be used as reducing agents for photographic material in the production of dry photographic copies on a layer essentially containing non-photosensitive reducible silver salts, reducing agents and a toner and, optionally, a photosensitive heavy metal compound and/or a polymethine sensitiser for spectrally sensitising the non-photosensitive silver compound.

Materials and processes of this kind are described, for example, in German Pats. Nos. 1,300,014, 1,234,243, in U.S. Pat. Nos. 3,457,075, 3,619,237, in French Pat. No. 2,037,847 and Belgian Pats. Nos. 770,971, 771,274 and 771,730.

The acid-activated fuller's earth used in the following Examples was obtained from Sudchemie AG, Munich, under the name "K 10 SF", whilst the ion exchanger was produced in accordance with German Pat. No. 915,267.

EXAMPLE 1

A solution of 134 g (1 mol) of 4-isopropenylphenol in 200 ml of toluene is added dropwise with stirring at 100° C to a suspension of 20 g of an acid-activated fuller's earth in 100 ml of toluene. At the same time, 112 g (2 mols) of isobutylene are introduced. The mixture is then left to react for 3 hours at 100° C, after which the catalyst is filtered off, the solvent distilled off and the 223 g residue obtained fractionated.

30.2 g (0.16 mol) of 5-hydroxy-1,1,3,3-tetramethyl indane melting at 118° C are thus obtained at a boiling temperature of 144° C/12 Torr, and 133 g (0.54 mol) of 5-hydroxy-6-tert.-butyl-1,1,3,3-tetramethyl indane melting at 114° C at a boiling temperature of 153° C/12 Torr:

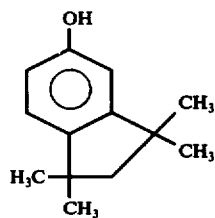
(I)

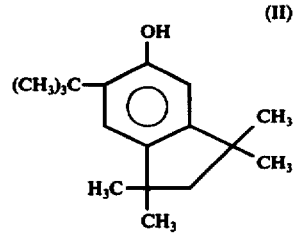
(II)

EXAMPLE 2

A solution of 134 g of 4-isopropenylphenol in 100 ml of tert.-butanol and 100 ml of benzene is added dropwise with stirring at the boiling temperature at a suspension of 20 g of an acid-activated fuller's earth, the water of reaction formed being azeotropically distilled off. After the water has been separated from the azeotrope, the solvent is returned to the reaction mixture. On completion of the addition, the mixture is left to react for another 3 hours. After the catalyst has been filtered off, the solvent is distilled off and the 179 g residue fractionated. 5-Hydroxy-1,1,3,3-tetramethyl indane is thus obtained in a yield of 121.2 g (64% of the theoretical), and 5-hydroxy-6-tert.-butyl-1,1,3,3-tetramethyl indane in a yield of 27 g (11% of the theoretical).

EXAMPLE 3

30.4 g (0.2 mol) of 2-hydroxy-2-(4-hydroxyphenyl)-propane are dissolved in 20 g (0.27 mol) of tert.-butanol and 30 ml of benzene. This solution is added dropwise with stirring over a period of 3 hours at the boiling temperature to a suspension of 4 g of an acid-activated fuller's earth in 20 ml of benzene, the water of reaction formed being simultaneously distilled off azeotropically. After the water has been separated from the azeotrope, the solvent which is left is returned to the reaction mixture. The reaction mixture is then left to react for another 2 hours at boiling temperature. The catalyst is then filtered off and the solvent distilled off. The 25.9 g residue has the following composition:

| | |
|---|---|
| First runnings | 20.02% by weight |
| 5-Hydroxy-1,1,3,3-tetramethyl indane | 57.19% by weight |
| Intermediate runnings | 4.53% by weight |
| 5-Hydroxy-1,1,3,3-tetramethyl-6-tert.-butyl indane | 18.26% by weight |

EXAMPLE 4

A solution of 67 g (0.25 mol) of dimeric 4-isopropenylphenol in 100 g of tert.-butanol and 50 ml of benzene is added dropwise with stirring over a period of 3 hours at the boiling temperature to a suspension of 20 g of an acid-activated fuller's earth in 100 ml of benzene, the water formed being simultaneously distilled off azeotropically. After the water has been separated from the distillate, the solvent is returned to the reaction mixture. The catalyst is then filtered off and the solvent distilled off, leaving a 113.1 g residue of the following composition:

| | |
|---|---|
| Unknown compounds | 5.24% by weight |
| Intermediate runnings | 0.39% by weight |
| 5-Hydroxy-1,1,3,3-tetramethyl indane (56% of the theoretical) | 46.74% by weight |
| Intermediate runnings | 0.24% by weight |
| 5-Hydroxy-1,1,3,3-tetramethyl-6-tert.-butyl indane (42% of the theoretical) | 46.34% by weight |
| Last runnings | 1.06% by weight |

EXAMPLE 5

A solution of 134 g (1mol) of dimeric 4-isopropenylphenol in 200 ml of tert.-butanol and 100 ml of benzene is added dropwise with stirring over a period of 3 hours at the boiling temperature to a mixture of 200 ml of benzene and 6 ml of concentrated sulphuric acid, the water formed being distilled off azeotropically. The solvent is returned to the reaction mixture after separation of the water from the distillate. The catalyst is then washed out with 10% by weight aqueous sodium hydrogen carbonate solution. The solvent is distilled off from the benzene solution. The residual crude mixture weighing 214.4 g is subjected to fractional distillation, giving 59.8 g (0.31 mol) of 5-hydroxy-1,1,3,3-tetramethyl indane and 49.4 g (0.20 mol) of 5-hydroxy-6-tert.-butyl-1,1,3,3-tetramethyl indane.

EXAMPLE 6

134 g of dimeric 4-isopropenylphenol, 20 g of an acid-activated fuller's earth and 112 g of isobutylene are introduced into an autoclave, and the autoclave is closed. The contents of the autoclave are then heated with stirring to around 180° C and left at that temperature for 6 hours. After cooling to room temperature, 100 ml of toluene are added to the reaction mixture, the catalyst filtered off and the toluene distilled off, leaving 266 g of a crude mixture from which 124 g (65% of the theoretical) of 5-hydroxy-1,1,3,3-tetramethyl indane and 25.4 g (10% of the theoretical) of 5-hydroxy-6-tert.-butyl-1,1,3,3-tetramethyl indane are obtained by fractional distillation.

EXAMPLE 7

150 g (1 mol) of 4-tert.-butylphenol and 400 g of an acid-activated fuller's earth are introduced into an autoclave. 1650 g (29.5 mol) of isobutylene and 2600 g (9.7 mol) of molten dimeric 4-isopropenylphenol are then simultaneously pumped in over a period of about 4 to 5 hours at a temperature of around 180° C. The mixture is then left to react for 4 hours at around 180° C. The hot reaction mixture is then filtered off from the catalyst under suction, 4184 g of crude product being obtained in this way. Fractional distillation gives 1980 g (10.4 mol) of 5-hydroxy-1,1,3,3-tetramethyl indane and 564 g (2.3 mol) of 5-hydroxy-6-tert.-butyl-1,1,3,3-tetramethyl indane.

EXAMPLE 8

A solution of 67 g (0.25 mol) of dimeric 4-isopropenylphenol, 45 g (0.64 mol) of 2-methyl-2-butene and 150 ml of benzene is added dropwise with stirring over a period of 4 hours at the boiling temperature to a suspension of 20 g of an acid-activated fuller's earth in 50 ml of benzene. After stirring for another 4 hours at the boiling temperature, the catalyst is filtered off and the solvent distilled off. The residue obtained of 87.4 g is subjected to fractional distillation. Recrystallisation from benzene of the fraction boiling at 159°-170° C/12 Torr gives 17.3 g (0.025 mol) of 5-hydroxy-1,1,3,3-pentamethyl indane (III) melting at 149° C.

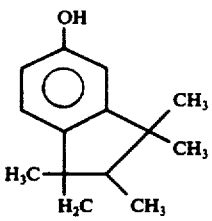

(III)

EXAMPLE 9

134 g (0.5 mol) of molten dimeric 4-isopropenylphenol and 120 g (1.07 mol) of diisobutylene are simultaneously added dropwise over a period of 4 hours at around 90° C to a suspension of 20 g of an acid-activated fuller's earth in 100 ml of toluene. The mixture is then left to react for another 2 hours at 90° C, after which the catalyst is filtered off and the solvent distilled off. Fractional distillation of the residue gives a fraction which distills over at 160°-170° C/12 Torr and subsequently solidifies in crystalline form. Recrystallisation from petroleum ether gives 41.2 g (34% of the theoretical) of 5-hydroxy-1,1,3-trimethyl-3-neopentyl indane (IV) melting at 102° C.

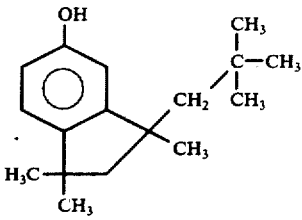

(IV)

EXAMPLE 10

57 g (0.25 mol) of 2,2-bis-(4-hydroxyphenyl)-propane, 10 g of an acid-activated fuller's earth and 84 g (0.75 mol) of diisobutylene are stirred in an autoclave for 8 hours at around 150° C. The catalyst is then filtered off and the reaction mixture subjected to fractional distillation, giving 25.2 g (44% of the theoretical) of 5-hydroxy-1,1,3-trimethyl-3-neopentyl indane.

EXAMPLE 11

121 g (0.5 mol) of 2,2-bis-(4-hydroxyphenyl)-butane, 22 g of an acid-activated fuller's earth and 90 g (1.6 mol) of isobutylene are stirred in an autoclave for 6 hours at 180° C. After cooling, the reaction mixture is taken up in 150 ml of toluene, the catalyst filtered off and the solvent evaporated. The residue is fractionated through a 1 meter glass-packed column, giving at a boiling temperature of 155° to 160° C/12 Torr 37 g of a fraction from which 24.8 g (20% of the theoretical) of 5-hydroxy-1,3,3-trimethyl-1-ethyl indane (V) melting at 86° C are obtained by recrystallisation from 90 ml of petroleum ether.

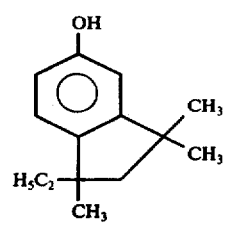

(V)

EXAMPLE 12

144 g (0.54 mol) of 1,1-bis(4-hydroxyphenyl)-cyclohexane, 22 g of an acid-activated fuller's earth and 90 g (1.6 mol) of isobutylene are stirred in an autoclave for 6 hours at 180° C. After cooling, the reaction mixture is taken up in 150 ml of toluene, the catalyst filtered off and the solvent evaporated, leaving 224 g of a crude mixture which is subjected to fractional distillation, giving at a boiling temperature of 144°-146° C/1.2 Torr 48 g of a fraction from which 24.5 g (0.11 mol) of 5-hydroxy-1,1-pentamethylene-3,3-dimethyl indane (VI) melting at 104° C are obtained by recrystallisation from 110 ml of petroleum ether.

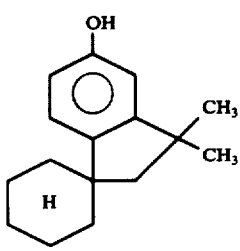

(VI)

EXAMPLE 13

114 g (0.5 mol) of 2,2-bis-(4-hydroxyphenyl)-propane, 6 ml of concentrated sulphuric acid and 90 g (1.6 mol) of isobutylene are stirred in an autoclave for 6 hours at 180° C. After cooling, the reaction product is taken up in 150 ml of toluene and washed with 10% by weight aqueous sodium hydrogen carbonate solution to remove the catalyst. The toluene solution is then distilled to remove the solvent and the residue of 176.9 g is subsequently subjected to fractional distillation, giving 20.6 g (22% of the theoretical) of 5-hydroxy-1,1,3,3-tetramethyl indane.

EXAMPLE 14

750 g (5 mol) of 4-tert.-butylphenol and 320 g of an acid-activated fuller's earth are introduced into a 10 liter autoclave and heated to 180° C. 1960 g (35 mol) of isobutylene and 3420 g (15 mol) of molten 2,2-bis-(4-hydroxyphenyl)-propane are simultaneously pumped in over a period of 4 to 5 hours at the aforementioned temperature. The mixture is then left to react with stirring for another 4 hours at 180° C. The hot reaction mixture is then filtered off from the catalyst, giving 6100 g of a crude mixture from which 2230 g (11.7 mol) of 5-hydroxy-1,1,3,3-tetramethyl indane are obtained by fractional distillation.

EXAMPLE 15

500 g of a crude mixture of the following composition:

| First runnings: | 2.28 % by weight |
|---|---|
| 4-Tert.-butylphenol | 31.11 % by weight |
| Intermediate runnings I | 1.35 % by weight |
| 5-Hydroxy-1,1,3,3-tetramethyl indane | 25.70 % by weight |
| 2,4-Di-tert.-butylphenol | 14.20 % by weight |
| Intermediate runnings II | 14.37 % by weight |
| 5-Hydroxy-1,1,3,3-tetramethyl-6-tert.-butyl indane | 8.20 % by weight |
| Last runnings | 2.79 % by weight | in which the first runnings, intermediate runnings I and II and final runnings were not identified, were heated with stirring for 5 hours to 180° C with 30 g of an acid-activated fuller's earth. The gas escaping was collected in a cold trap at around −60° C, giving 61 g of isobutylene. The hot reaction mixture was then filtered off from the catalyst giving 410 g of a product of the following composition:

| Phenol | 13.27 % by weight |
|---|---|
| 4-Tert.-butylphenol | 29.23 % by weight |
| Intermediate runnings I | 1.27 % by weight |
| 5-Hydroxy-1,1,3,3-tetramethyl indane | 35.30 % by weight |
| 2,4-Di-tert.-butylphenyl | 1.65 % by weight |
| Intermediate runnings II | 7.17 % by weight |
| Final runnings | 12.10 % by weight | in which intermediate runnings I and II and the last runnings were not identified.

EXAMPLE 16

250 g of the mixture used as starting product in Example 15 are heated for 5 hours to 175° C with 25 g of an acid-acitivated fuller's earth and 500 g of phenol. The hot reaction mixture is filtered off from the catalyst and has the following composition:

| Phenol | 71.18 % by weight |
|---|---|
| 4-Tert.-butylphenol | 17.80 % by weight |
| Intermediate runnings I | 0.52 % by weight |
| 5-Hydroxy-1,1,3,3-tetramethyl indane | 7.15 % by weight |
| 2,4-Di-tert.-butylphenol | 0.52 % by weight |
| Intermediate runnings II | 1.74 % by weight |
| Last runnings | 1.07 % by weight | in which the intermediate runnings I and II and the last runnings were not identified.

EXAMPLE 17

A molten mixture of 575 g (2.5 mol) of 2,2-bis-(4-hydroxyphenol)-propane and 1875 g (12.5 mol) of 4-tert.-butylphenol was pumped with stirring over a period of 4 to 5 hours at 180° C into 225 g (1.5 mol) of 4-tert.-butylphenol and 125 g of an acid-activated fuller's earth accommodated in an autoclave. This was followed by stirring for another 4 hours at 180° C. The hot reaction mixture was then filtered off from the catalyst and the resulting 2621 g of reaction mixture subjected to fractional distillation, giving 380 g (80% of the theoretical) of 5-hydroxy-1,1,3,3-tetramethyl indane.

EXAMPLE 18

172 g (1.15 mol) of 4-tert.-butylphenol, 57.5 g (0.25 mol) of 2,2-bis-(4- hydroxyphenyl)-propane and 5 g of boron trifluoride etherate are stirred in an autoclave for 6 hours at around 150° C. The reaction mixture is then diluted with 400 ml of toluene and the catalyst washed out with 900 ml of water used in several portions. The solvent is then distilled off. 17.6 g (0.095 mol) of 5-hydroxy-1,1,3,3-tetramethyl indane were isolated from the 216.7 g reaction product by fractional distillation.

EXAMPLE 19

172 g (1.15 mol) of 4-tert.-butylphenol, 57.5 g (0.25 mol) of 2,2-bis-(4-hydroxyphenyl)-propane and 20 g of an ion exchanger are heated with stirring for 5 hours to about 170° C is an autoclave. The ion exchanger is then filtered off while still hot, leaving 208.5 g of a reaction mixture from which 16.7 g (0.088 mol) of 5-hydroxy-1,1,3,3-tetramethyl indane are isolated by fractional distillation.

EXAMPLE 20

30 g (0.088 mol) of 2,2,-bis(4-hydroxy-3-tert.-butylphenyl)-propane and 3 g of an acid-activated fuller's earth and stirred for 4 hours at 180° C in an autoclave. After cooling, the reaction mixture is diluted with 150 ml of toluene, filtered off from the catalyst under suction and the solvent distilled off. The reaction mixture has the following composition:

| Phenol | 10.95 % by weight |
|---|---|
| 4-Tert.-butylphenol | 31.45 % by weight |
| Intermediate runnings I | 3.93 % by weight |
| 5-Hydroxy-1,1,3,3-tetramethyl indane | 30.01 % by weight |
| 2,4-Di-tert.-butylphenol | 4.73 % by weight |

| | |
|---|---|
| Intermediate runnings II | 2.64 % by weight |
| 5-Hydroxy-1,1,3,3-Tetramethyl-6-tert.-butyl indane | 3.58 % by weight |
| Last runnings | 16.21 % by weight | in which the last runnings and intermediate runnings I and II were not identified.

EXAMPLE 21

172.5 g (1.15 mol) of 4-tert.-butylphenol, 57.5 g (0.25 mol) of 2,2-bis-(4-hydroxyphenyl)-propane and 10 g of an acid-activated fuller's earth were heated with stirring in an autoclave for 6 hours to approximately 200° C. The hot reaction mixture is then filtered off from the catalyst under suction and the resulting 221.3 g reaction mixture subjected to fractional distillation in vacuo, giving 25.2 g (52% of the theoretical) of 5-hydroxy-1,1,3,3-tetramethyl indane.

EXAMPLE 22

172.5 g of 4-tert.-butylphenol, 57.5 g of 2,2-bis-(4-hydroxyphenyl)-propane and 20 g of p-toluene sulphonic acid are stirred in an autoclave for 6 hours at around 180° C. After cooling, the reaction mixture is repeatedly washed with about 250 ml of 10% by weight aqueous sodium hydrogen carbonate solution to remove the catalyst, and then subjected to fractional distillation in vacuo. 9.3 g (0.05 mol) of 5-hydroxy-1,1,3,3-tetramethyl indane are isolated from 157.7 g of reaction mixture.

EXAMPLE 23

114 g (0.5 mol) of 2,2-bis-(4-hydroxyphenyl)-propane, 90 g (1.6 mol) of isobutylene and 25 g of an aluminum silicate are stirred in an autoclave for 6 hours at around 300° C under the naturally prevailing pressure. The catalyst is then filtered of while still hot. 41.8 g (44% of the theoretical) of 5-hydroxy-1,1,3,3-tetramethyl indane are isolated by fractional distillation in vacuo from the 170.9 g of reaction mixture.

EXAMPLE 24

1680 g (30 mol) of isobutylene are pumped over a period of 4 to 5 hours at a pressure of 1 atmosphere into a mixture of 2300 g (10.1 mol) of 2,2-bis-(4-hydroxyphenyl)-propane, 750 g (5 mol) of 4-tert.-butylphenol and 250 g of an acid-activated fuller's earth accommodated in an autoclave. The initial temperature of 100° C is reduced to 65° C after 1-2 hours. This is followed by heating for 6 hours to around 180° C with continued stirring. The hot catalyst is then filtered off from the resulting 4600 g of reaction mixture from which 463 g (2.43 mol) of 5-hydroxy-1,1,3,3-tetramethyl indane are isolated by fractional distillation in vacuo.

EXAMPLE 25

99 g (0.33 mol) of 2,2-bis-(4-hydroxy-3-chlorphenyl)-propane, 20 g of an acid-activated fuller's earth and 60 g (1.07 mol) of isobutylene are introduced into an autoclave. After stirring for 6 hours at 230° C, 200 ml of toluene are added, the catalyst is filtered off and the solvent evaporated. The residue (127.1 g) is distilled in vacuo in a packed column. 12.2 g (0.055 mol) of 5-hydroxy-6-chlor-1,1,3,3-tetramethyl indane (VII) melting at 51° C are obtained from the fraction boiling at 75°-83° C/0.2 Torr by recrystallisation from 25 ml of petroleum ether.

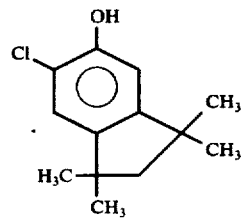

(VII)

EXAMPLE 26

A mixture of 142 g (0.5 mol) of 2,2-bis-(4-hydroxy-3,6-dimethylphenyl)-propane and 375 g (2.5 mol) of 4-tert.-butylphenol is added dropwise over a period of 4 hours at 180° C to 65 g of tert.-butylphenol and 30 g of an acid-activated fuller's earth. The mixture is then stirred for 4 hours at 180° C. The reaction mixture is dissolved in 900 ml of toluene, the fuller's earth filtered off under suction and the solvent distilled off. The residue (467 g) is subjected to fractional distillation. 24.1 g (0.11 mol) of 5-hydroxy-1,2,3,3,4,6-hexamethyl indane (VIII) melting at 55° to 57° C are obtained from the fraction boiling at 140° to 150° C/12 Torr by recrystallisation from 90 ml of petroleum ether.

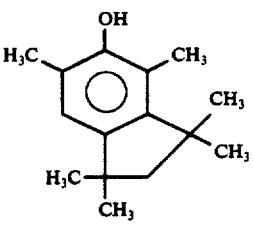

(VIII)

What is claimed is:

1. Process for producing 1,1,3,3-substituted hydroxy indanes which comprises reacting an alkylphenol having the formula

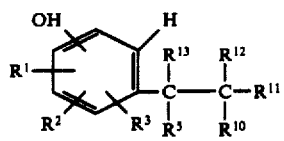

wherein $R^1$, $R^2$ and $R^3$, which may be the same or different, are selected from the group of hydrogen, halogen, alkyl with up to 12 carbon atoms, cycloalkyl with 3 to 8 carbon atoms, aralkyl with up to 6 carbon atoms in the alkyl portion and up to 14 carbon atoms in the aryl portion, phenyl, naphthyl, anthryl, and the foregoing substituted by alkyl with up to 12 carbon atoms, in addition to which $R^2$ and $R^3$, when they are in the ortho position relative to one another may be taken together with the carbon atoms of the benzene ring to which they are attached to form a 5-membered carbocylic ring, $R^5$ is selected from the group of alkyl with up to 12 carbon atoms, cycloalkyl with 3 to 8 carbon atoms, aralkyl with up to 6 carbon atoms in the alkyl portion and up to 14 carbon atoms in the aryl portion, phenyl, naphthyl, anthryl, and the foregoing substituted by alkyl with up to 12 carbon atoms, $R^{10}$ and $R^{11}$ which may be the same or different, are selected from the group of hydrogen and alkyl with up to 12 carbon atoms, cycloalkyl with 3 to 8 carbon atoms, aralkyl with up to 6 carbon atoms in the alkyl portion and up to 14 carbon atoms in the aryl portion, phenyl, naphthyl, anthryl, and the foregoing substituted by alkyl with up to 12 carbon atoms, in addition to which $R^5$ and $R^{10}$ may form a cycloaliphatic ring with the carbon atoms to which they are attached, $R^{12}$ is hydrogen, and $R^{13}$ is halogen, hydroxyphenyl or —$OR^{14}$ where $R^{14}$ is selected from the group of hydrogen and alkyl with up to 12 carbon atoms, cycloalkyl with 3 to 8 carbon atoms, aralkyl with up to 6 carbon atoms in the alkyl portion and up to 14 carbon atoms in the aryl portion, phenyl, naphthyl, anthryl, and the foregoing substituted by alkyl with up to 12 carbon atoms, in addition to which $R^{12}$ and $R^{13}$ together may also represent another bond between the carbon atoms to which they are attached, with 2 moles, per mole of said alkylphenol, of an olefin containing the following group,

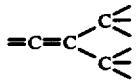

in which at least one double-bonded carbon atom contains only carbon-to-carbon bonds, or with a compound which yields the corresponding olefin in situ, in the presence of an acid catalyst at a temperature in the range from 70° to 360° C.

2. Process of claim 1 wherein the reaction is carried out at a temperature in the range from 100° to 250° C.

3. Process of claim 1 wherein an alcohol is used as the compound yielding the corresponding olefin in situ.

4. Process of claim 1 wherein a tert.-alkyl phenol is used as the compound yielding the corresponding olefin in situ.

5. Proccess of claim 1 wherein the olefin is isobutylene.

6. Process of claim 3 wherein the alcohol is tert.-butanol.

7. Process of claim 4 wherein the tert.-alkylphenol is tert.-butyl phenol.

8. Process of claim 4 wherein the same tert.-alkylphenol is used for said alkylphenol and for the tert.-alkylphenol.

9. Process of claim 1 wherein the alkylphenol is 4-isopropenylphenol, 2,2-bis-(4-hydroxyphenyl)-propane, 2,2-bis-(4-hydroxy-3,5-dimethylphenyl)-propane or the dimer of 4-isopropenylphenol.

* * * * *